(12) United States Patent
Nickol et al.

(10) Patent No.: US 9,642,977 B2
(45) Date of Patent: May 9, 2017

(54) HOLLOW STRUCTURE FOR RESPIRATORY MASK CUSHION

(71) Applicant: ResMed R&D Germany GmbH, Martinsried (DE)

(72) Inventors: Johannes Nickol, Munich (DE); Jens Rothfuss, Munich (DE); Sebastian Burz, Germaringen (DE); Robert Eibl, Bad Toelz (DE); Bernd Lang, Graefelfing (DE)

(73) Assignee: ResMed Limited, Bella Vista (AU)

( * ) Notice: Subject to any disclaimer, the term of this patent is extended or adjusted under 35 U.S.C. 154(b) by 775 days.

(21) Appl. No.: 13/963,073

(22) Filed: Aug. 9, 2013

(65) Prior Publication Data

US 2014/0044905 A1 Feb. 13, 2014

Related U.S. Application Data

(60) Provisional application No. 61/681,796, filed on Aug. 10, 2012.

(51) Int. Cl.
*A61M 16/06* (2006.01)
*B29D 22/00* (2006.01)

(52) U.S. Cl.
CPC ........ *A61M 16/06* (2013.01); *A61M 16/0622* (2014.02); *B29D 22/00* (2013.01); *Y10T 428/1352* (2015.01)

(58) Field of Classification Search
CPC ... A61M 16/06; A61M 16/0622; B29D 22/00; Y10T 428/1352
See application file for complete search history.

(56) References Cited

U.S. PATENT DOCUMENTS

| 5,142,820 | A | * | 9/1992 | Aquino | A47G 7/07 |
| | | | | | 47/41.12 |
| 5,219,360 | A | | 6/1993 | Georgiade | |
| 2008/0289633 | A1 | | 11/2008 | Kwok et al. | |
| 2015/0047644 | A1 | * | 2/2015 | Baiko | A61M 16/06 |
| | | | | | 128/206.26 |

FOREIGN PATENT DOCUMENTS

| WO | WO 2009/065368 | 3/2009 |
| WO | WO 2009/062265 | 5/2009 |
| WO | WO 2009/143586 | 12/2009 |

* cited by examiner

*Primary Examiner* — Michael C Miggins
(74) *Attorney, Agent, or Firm* — Nixon & Vanderhye P.C.

(57) ABSTRACT

The present invention provides a method for producing a filled hollow structure, preferably a cushion for a breathing mask. According to said method, a hollow structure of a first material having a cavity is produced, wherein the hollow structure has an inlet to and an outlet from the cavity. The hollow structure is positioned on a tool for holding the hollow structure. Subsequently a second material is inserted through the inlet into the cavity, while gas present in the cavity can escape through the outlet. Finally, the inlet and/or the outlet is sealed. During the step of inserting the second material through the inlet into the cavity the outlet resists flow of said second material.

41 Claims, 4 Drawing Sheets

SEE DETAIL
FIG.3C

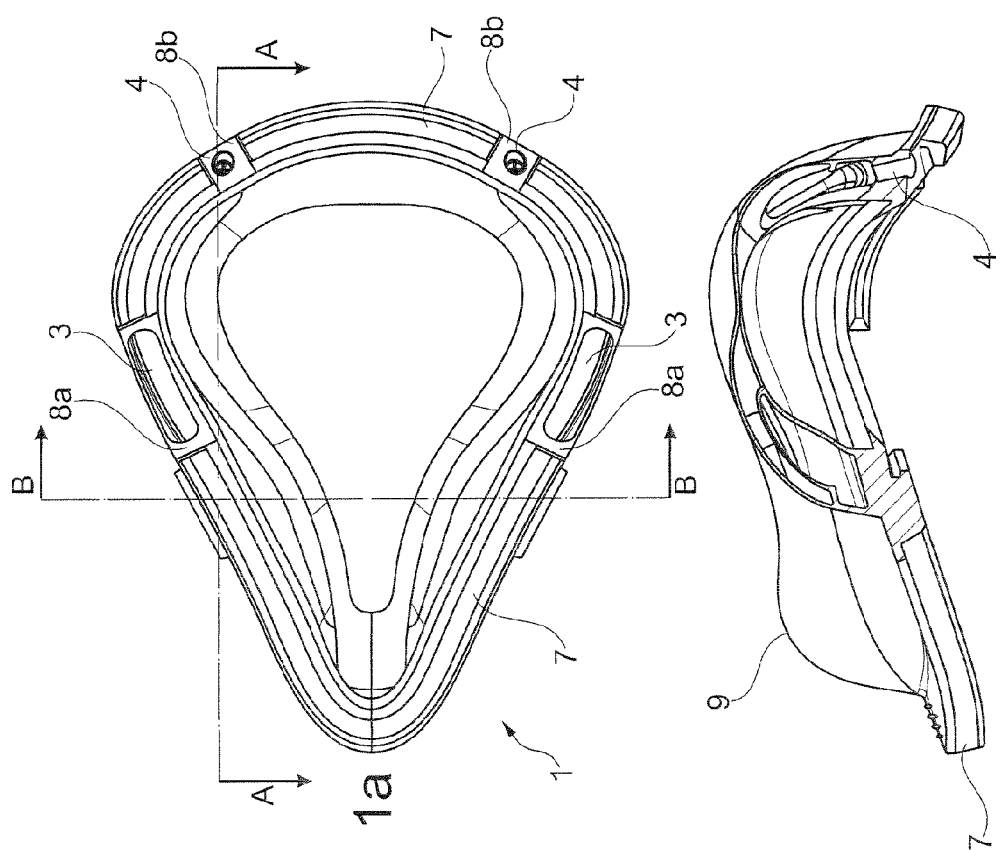

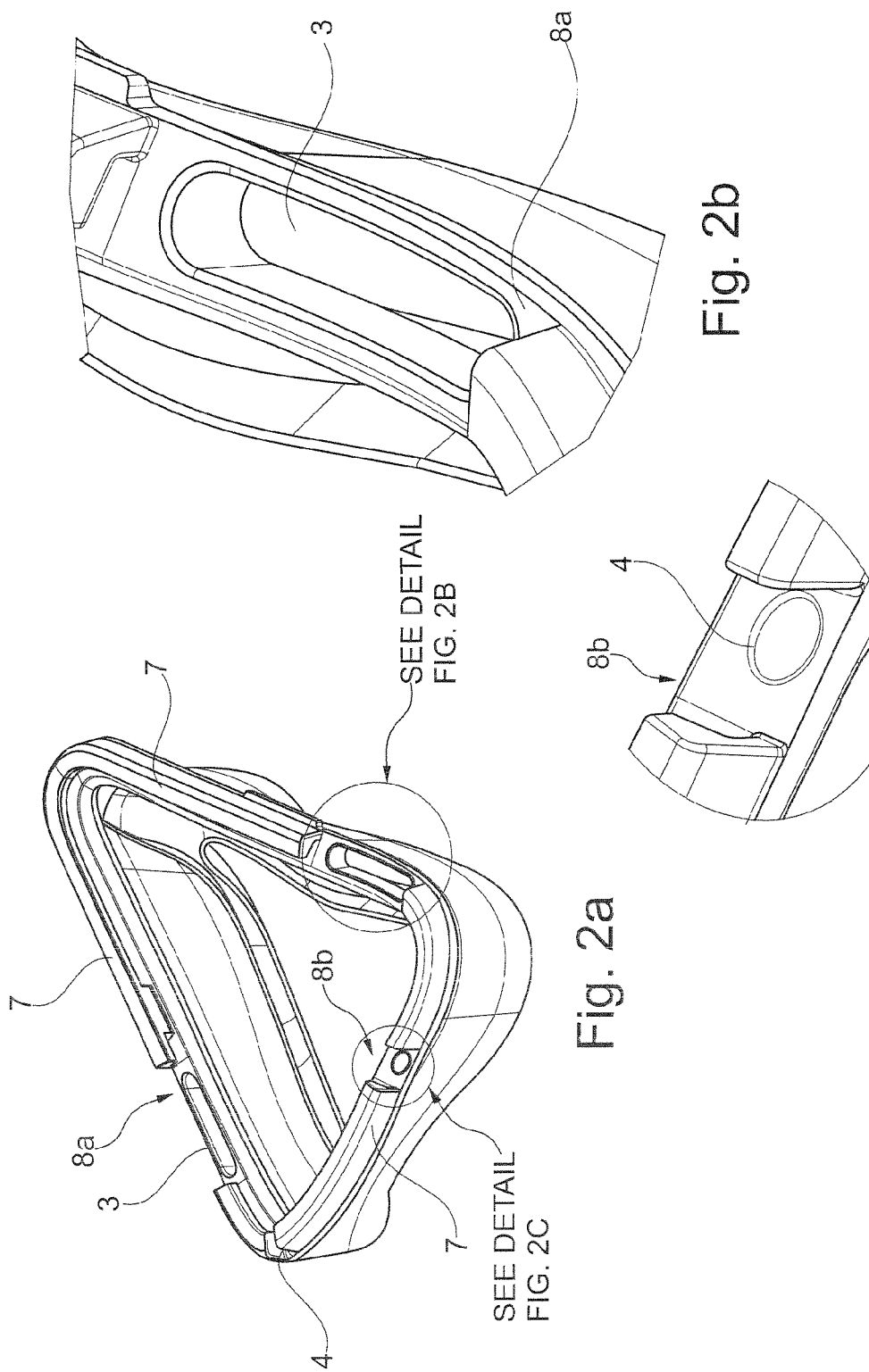

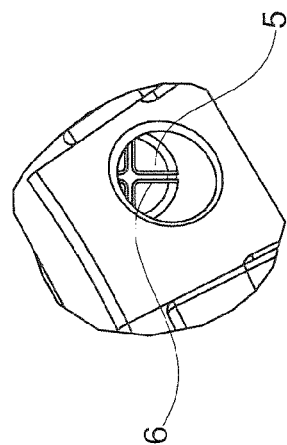
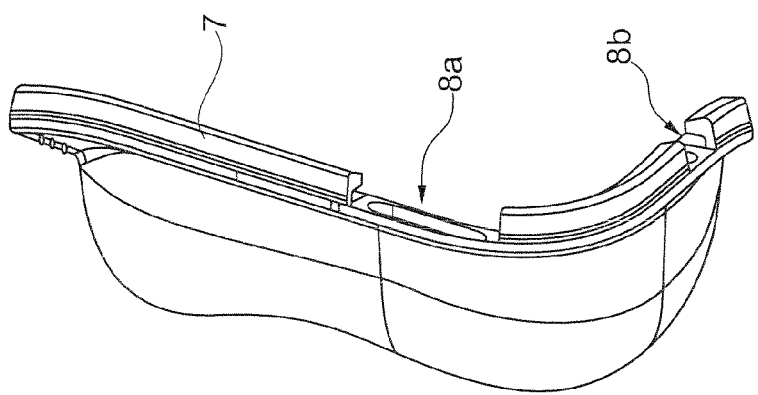
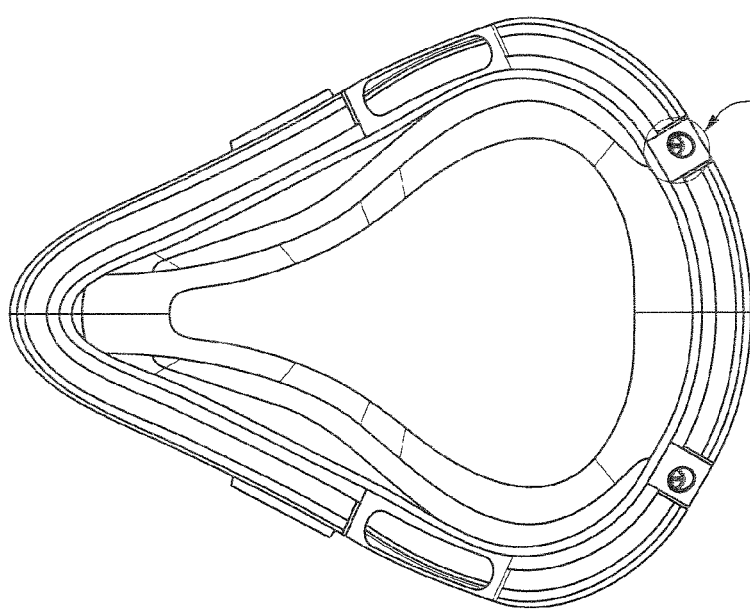
Fig. 3c
Fig. 3b
Fig. 3a

HOLLOW STRUCTURE FOR RESPIRATORY MASK CUSHION

CROSS-REFERENCE TO RELATED APPLICATION

This application claims the benefit of Provisional Application No. 61/681,796, filed Aug. 10, 2012, the entire content of which is hereby incorporated by reference in this application.

The present invention relates to a hollow structure for a cushion for a respiratory mask as well as to a method for producing a filled hollow structure for a respiratory mask.

A variety of respiratory masks is known in the prior art. One type of respiratory mask consists to a certain extent of a first material such as silicone and comprises a pocket which is filled with a softer second material such as a gel. For example, WO 2009/065368 A1 describes an upper mask part of a respiratory mask which is produced from an elastic material having varying wall thickness levels of the walls over the course of the cross-section thereof. The upper mask part is connected to a mask body by a mask connecting region on the side facing away from the patient's face. The respiratory mask has inwardly formed, thin peripheral contact lips on the side facing the patient's face. At least one region shaped from a filling material is introduced in or on the walls of the upper mask part. In order to introduce the filling material in the walls of the upper mask part the upper mask part comprises an opening which may be closed after introducing the filling material by means of gluing, soldering or applying a plug.

However, introducing a filling material in the wall of an upper mask part as described in WO 2009/065368 A1 may be quite demanding depending on the shape of the cavity or pocket to be filled with the filling material. For example, if the shape of the cavity is somewhat tortuous the filling material may not reach each and every portion of the cavity to be filled. Moreover, a tortuous filling path may cause the formation of air bubbles which may lead to an inferior mask quality. Such air bubbles not only affect the elastic properties of the filling material and consequently of the entire mask, but are also aesthetically less pleasing.

It is therefore an object of the present invention to provide a method for manufacturing a cushion for a respiratory mask being filled with a filling material which overcomes the above mentioned disadvantages of the prior art. It is another object of the present invention to provide a hollow structure which may be filled in order to produce a cushion for respiratory mask avoiding the above mentioned problems.

These objects are achieved with the subject-matter of the independent claims. Preferred features are described in the dependent claims.

The present invention inter alia provides a method for producing a filled hollow structure, preferably a cushion for a breathing mask. According to said method, a hollow structure of a first material having a cavity is produced, wherein the hollow structure has an inlet to and an outlet from the cavity. The hollow structure is positioned on a tool for holding the hollow structure. Subsequently a second material is inserted through the inlet into the cavity, while gas present in the cavity can escape through the outlet. Finally, the inlet and/or the outlet is sealed. During the step of inserting the second material through the inlet into the cavity the outlet resists flow of said second material.

The resistance of the outlet is to be understood in such a manner that the outlet resists flow of the second material if typical or standard process parameters are applied during insertion of the second material into the cavity. In other words, if the process of inserting the second material into the cavity is driven under normal conditions, only a minor, preferably negligible, amount of material escapes the cavity through the outlet. For example, in the context of the present invention the outlet would still be considered to resist flow of the second material if during the entire step of inserting the second material into the cavity a single droplet of the second material is formed beyond the outlet. It is, however, preferred that the outlet entirely prevents the flow of the second material during insertion into the cavity. In other words, it is preferred that the outer surface of the hollow structure surrounding the outlet remains pristine during insertion of the second material into the cavity.

Preferably, the inlet and/or the outlet comprise a membrane, which is preferably adapted to be punctured. Accordingly, the method preferably further comprises the step of puncturing the membrane before inserting the second material through the inlet. The membrane of the inlet may be punctured by means of the tool which is adapted to insert the second material through the inlet into the cavity. For this purpose, the injection tool preferably has a sharp tip in order to cut into the membrane.

The membrane of the inlet seals the cavity around the injection tool during insertion of the second material into the cavity. Moreover, when the injection tool is withdrawn from the cavity the membrane of the inlet may wipe off remains of the second material on the injection tool thus cleansing the injection tool.

The membrane of the outlet may also be punctured by means of the injection tool. However, another tool such as a needle or the like may be used in order to puncture the membrane of the outlet before inserting the second material through the inlet. The punctured membrane of the outlet preferably allows for venting, yet resists flow of the second material during insertion into the cavity. This may, e.g., be achieved by providing a sufficiently small hole in the membrane, which is large enough to allow for venting, yet small enough to prevent flow of the second material. In addition or alternatively the punctured or ruptured membrane may have a specific puncture or rupture shape. This may, e.g., be achieved by the membrane comprising a predetermined breaking point such as, e.g., a crossed slot, a cross recess, a weakened region or a perforation. Thus, after puncturing of the membrane, the membrane comprises an opening having a shape of, e.g., a crossed slot, which may allow for venting, yet resists flow of the second material during insertion into the cavity. Rather than puncturing the membrane, the membrane may also have a preformed orifice having a suitable shape, e.g., of a crossed slot. In other words, the opening or orifice of the membrane of the outlet may be premanufactured in such a manner as to allow for venting while resisting flow of the second material during insertion into the cavity. This may be advantageous in that no puncturing is required and, in that the orifice is clearly predetermined and does not depend on the accuracy of the puncturing step.

The membrane of the inlet preferably also has a predetermined breaking point or an orifice as described above with respect to the outlet. Yet, the membrane of the inlet is preferably adapted and optimized for sealing the injection tool during insertion of the second material and/or for wiping off the injection tool during retraction.

The properties of the membrane having the orifice or the punctured membrane of the outlet may strongly depend on the specific process parameters used during insertion of the second material. However, it is generally preferred that the (punctured) membrane prevents flow of the second material if exposed to a pressure up to 3 hPa, preferably up to 5 hPa. It is also generally preferred that the (punctured) membrane prevents flow of a material having a viscosity in the range between 50 and 2000 MPas, preferably between 100 and 1100 MPas at 25° C. (DIN EN ISO 3219) if exposed to a pressure up to 3 hPa, preferably up to 5 hPa. It is also preferred that the flow rate of a material having a viscosity in a range between 50 and 2000 MPas, preferably between 100 and 1100 MPas, at 25° C. (DIN EN ISO 3219) if exposed to a pressure up to 3 hPa, preferably up to 5 hPa, through the (punctured) membrane is smaller than 100 $mm^3$/s, preferably smaller than 10 $mm^3$/s.

Preferably, the membrane has a diameter of less than 5 mm, preferably of less than 4 mm, more preferably of less than 3 mm. Preferably, the membrane has a surface of less than 20 $mm^2$, preferably of less than 13 $mm^2$, more preferably of less than 7 $mm^2$. It is further preferred that the orifice of the membrane or the opening in the membrane created by puncturing the membrane has a diameter of less than 4 mm, preferably of less than 3 mm, more preferably of less than 2 mm. It is also preferred that the orifice of the membrane or the opening in the membrane created by puncturing the membrane has a surface of less than 13 $mm^2$, preferably of less than 7 $mm^2$, or more preferably of less than 3 $mm^2$.

The second material preferably has a viscosity in the range between 50 and 2000 MPas, preferably between 100 and 1100 MPas, at 25° C. (DIN EN ISO 3219).

It is further preferred that the inserted second material is distributed within the cavity by means of gravity, preferably by means of gravity only. In this regard, it is preferred that the hollow structure is pivoted or tilted during inserting the second material in order to completely fill the cavity with the second material. For example, the hollow structure may be pivoted or tilted up to +/−30°, preferably up to +/−60° with respect to a horizontal configuration of the hollow structure. Preferably, the hollow structure is not constantly pivoted or tilted at a specific angle. Rather, the inventive method preferably comprises the step of providing a predetermined "tilting path" which the hollow structure undergoes during inserting the second material. The tilting path evidently depends on the shape of the cavity of the hollow structure. Thus, it may be ensured that the inserted material is distributed by means of gravity into each and every portion of the said cavity leaving no air bubbles behind. The tilt angle may also be strongly asymmetric. It is, e.g., preferred that the cavity is filled during a first filling step at a tilt angle between 40° and 70°, preferably between 50° and 60°, and subsequently during a second filling step at a tilt angle of between −3° and −15°; preferably between −5° and −10°.

The method preferably further comprises the step of sealing the inlet and/or the outlet by curing and/or hardening the second material. Such sealing may be enhanced or accelerated by applying heat and/or UV radiation. In addition or alternatively the method preferably comprises the step of sealing the inlet and/or the outlet by applying a sealing material, preferably one or a combination of silicone, polyurethane and thermoplastic polymers.

Preferably, the first material consists of or comprises one or a combination of silicone, polysiloxane, silicone foam, silicone rubber and thermoplastic polymers. Preferably, the second material consists of or comprises one or a combination of gel, foam, liquid, gas, beads and silicone. It is preferred that the shore hardness of the second material lies in the range of about 10 to 20 Shore 000, preferably between 11 and 19, and more preferably between 12 and 18, between 13 and 17, between 14 and 16, and also preferable of about 15, preferably according to ASTM D 2240.

The Shore hardness of the first material preferably lies in a range between about 1 and 60, preferably between 1 and 40, also preferably between 3 and 25 and most preferably between about 5 and 10 Shore A, also preferred between 20 and 60 Shore A preferably according to DIN 53505.

According to a further preferred embodiment, the filled hollow structure, preferably the cushioning element, has a Shore 000 hardness in the range of about 45 to 90. The second material, e.g. a gel, preferably silicone gel, preferably has a Shore 000 hardness in the range of about 45 to 90, preferably between about 50 and 90, and more preferably between about 50 and 80, between about 60 and 75, between about 50 and 70, and also preferable of between about 50 and 70. The first material preferably has a Shore A hardness in the range of 20 to 60.

It is further preferred that the method comprises the step of removing the hollow structure from the tool, preferably by using compressed air. Preferably, the second material is inserted into the cavity under pressure and/or vacuum.

While the method according to the present invention is particularly suitable for manufacturing a cushion for a breathing or respiratory mask, the inventive method may also be utilized for producing other filled hollow structures.

The present invention further provides a hollow structure, preferably for a cushion for a respiratory mask, made of a first material having a cavity. The structure comprises an inlet for inserting a second material into the cavity and an outlet for gas present in the cavity to escape, wherein the inlet and/or outlet comprises a membrane which is adapted to be punctured and/or which has an orifice. The punctured membrane and/or the orifice preferably have a structure adapted to bias the membrane to a closed position.

Preferably, the orifice has the shape of a crossed slot. Preferably, the membrane comprises a predetermined breaking point, preferably a crossed slot, a cross recess, a weakened region or a perforation.

The present invention further provides a hollow structure made of a first material having a cavity, the structure comprising an inlet for inserting a second material into the cavity and an outlet for gas present in the cavity to escape, wherein the inlet and/or outlet comprises a self-healing membrane.

The term "self-healing membrane" as used in the present disclosure refers to a membrane, or a portion thereof, which is adapted to allow, under certain circumstances, flow of a fluid, preferably of gas present in the cavity, to escape whereas the membrane remains closed for any flow of the second material and/or heals itself as soon as it comes into contact with the second material.

Preferably, the self-healing membrane is adapted to be punctured by a puncturing tool in such a manner as to allow for the puncture site to self-seal upon removal of the puncturing tool. In other words, the self-healing membrane is sufficiently elastic to contract around the puncture site so as to sufficiently close the puncture site to withhold any flow of the second material.

Preferably, the self-healing membrane is adapted to be punctured in such a manner as to allow for the puncture site to self-seal upon insertion of the second material into the cavity. Thus, upon being puncture the membrane allows flow of a fluid, preferably of gas present in the cavity, to escape from the cavity. However, once the second material inserted into the cavity reaches the puncture site of the self-healing membrane said puncture site provides sufficient resistance to the flow of the second fluid. Thus, the second material seals the puncture site when hardening. Even though, strictly speaking, the second material seals the puncture site, this solution is also considered to be encompassed by the term "self-healing".

Preferably, the self-healing membrane has an orifice which is adapted to self-seal upon insertion of the second material into the cavity. Thus, the orifice need not be punctured, yet has the same self-healing properties as discussed above.

As outlined previously, the punctured membrane and/or the orifice preferably has a structure adapted to bias the self-healing membrane to a closed position. Preferably, the orifice has the shape of a crossed slot. Preferably, the self-healing membrane comprises a predetermined breaking point, preferably a crossed slot, a cross recess, a weakened region or a perforation.

The use of the self-healing membrane of the present invention leads to manufacturing efficiency because no additional steps are required to close or seal openings which may be necessary to introduce material into a cavity. This allows for a less costly manufacturing of better quality gel masks. Moreover, using one or more such self-healing membranes allows for the potential of making much more complex shapes, because the self-healing membrane may stop the flow of an inserted material even against gravity.

The hollow structure according to the present invention may be utilized in the method according to the present invention described above. Moreover, all structural features described above with respect to the inventive method are preferably also employed in the inventive hollow structure.

The present invention further provides a cushion for a respiratory mask comprising a hollow structure as described above, wherein the cavity is filled with a second material.

The present invention further provides a cushion for respiratory mask. The cushion comprises a sealed hollow basically triangular structure adapted to fit over a patient's nose and/or mouth and made of a first material. The hollow structure comprises at least one cavity extending along a part of the circumference of the cushion. A first circumferential portion of the cavity is filled with a second material and a second circumferential portion of the cavity is filled with a third material, the third material being different from the second material. Preferably, the at least one cavity extends only along a part of the circumference of the cushion.

Preferably, the first and second portions abut each other at an interface, the interface being substantially perpendicular to the circumference of the cushion. It is preferred that the first and second portions abut each other at an interface, the interface being inclined with respect to the circumference of the cushion. Preferably the inclination angle ranges between 5° and 7°, preferably between 10° and 14°, more preferably between 20° and 30°.

It is further preferred that the triangular structure comprises a base adapted to be positioned below the patient's nose or mouth and two sides adapted to lie against the patient's nose and/or cheeks, wherein the sides meet at a cusp adapted to rest on the patient's nose bridge, and wherein each side of the structure comprises a cavity filled with the second and third material. Preferably, the filled cavities extend around the corners of the triangular structure into the base, wherein the cavities are preferably substantially L-shaped. Preferably, the first portion of each cavity is located proximate the cusp and the second portion of each cavity is located proximate the base of the triangular structure. Preferably, the second material has a shore hardness which is lower than the shore hardness of the filled material.

It is further preferred that the hollow structure comprises a contact surface for contacting the patient's skin, wherein at least a part of said contact surface is a structured surface. The structured surface preferably has a marbled, nerved, flaked or scaly structure and/or comprises grooves, depressions, cavities, ridges, notches and/or bulbs. Preferably, the first and second portions of the cavity form a uniform, continuous cavity. Preferably, the first and second portions of the cavity are separated from each other by a membrane, preferably by a silicone membrane.

Preferred embodiments of the present invention are further elucidated with reference to the following Figures.

FIG. 1a shows a top view of a preferred embodiment of a hollow structure for a cushion for a breathing mask.

FIG. 1b shows a cross-sectional front view of the embodiment shown in FIG. 1a along line B-B.

FIG. 1c shows a cross-sectional side view of the embodiment shown in FIG. 1a along line A-A.

FIG. 2a shows a perspective view of the embodiment shown in FIG. 1.

FIGS. 2b and 2c show details of the perspective view of FIG. 2a (four times magnified).

FIGS. 3a and 3b show top and side views of the embodiment of FIG. 1 respectively.

FIG. 3c shows a detail of the top view of FIG. 3a (four times magnified).

Figure 4:
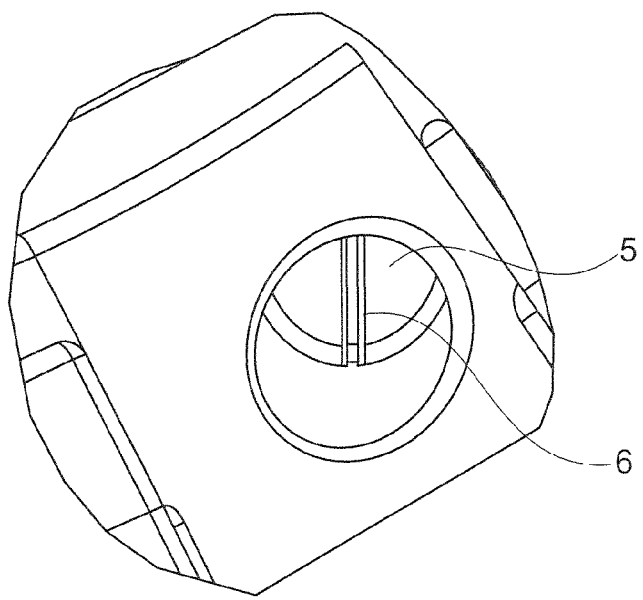
FIGS. 4 and 5 show a detail of alternative preferred embodiments, respectively (four times magnified).

FIG. 1a shows a preferred embodiment of a hollow structure 1 for a cushion for a respiratory mask. The hollow structure 1, which is made of a first material, preferably of silicone, has a cavity 2 as shown in FIG. 1b. The hollow structure 1 comprises two inlets 3 for inserting a second material such as a gel into the cavity 2 and two outlets 4 for gas present in the cavity 2 to escape. The hollow structure of the preferred embodiment comprises an edge 7 which is adapted to connect the cushion (once filled with the second material) with a respiratory mask. The edge 7 preferably comprises a connecting region for connecting the cushion to the mask, e.g. a recessed area such as, for example, an undercut. Said edge comprises two cut-outs or recess portions 8a in which the inlets 3 are formed as well as two cut-outs or recess portions 8b in which the outlets 4 are formed. Moreover, the hollow structure 1 comprises a lip 9 which is adapted to contact a user's face.

As shown in FIGS. 1a, 2a, 2b and 3a the inlets in the preferred embodiment have the shape of elongated ovals which are adapted to accommodate a tool for injecting the second material into the cavity 2. It will, however, be evident that other shapes and sizes for the inlets 3 may be chosen. Moreover, only a single inlet 3 may be provided or more than two inlets 3 such as three or four inlets may be provided in alternative embodiments. This may inter alia depend on the specific shape of the cavity or the cavities 2 within the hollow structure 1. In the case of the embodiment shown in the FIGS. the cavity surrounds a substantial portion of the circumference of the hollow structure 1. Thus, it may be difficult to fill the entire cavity 2 with the second material by means of a single inlet 3. Accordingly, two symmetrically arranged inlets 3 are provided in order to fill each half of a single cavity 2 or each of two cavities 2 via its own inlet 3.

As shown in FIG. 2b, the inlet 3 of the preferred embodiment does not comprise a membrane. Yet, alternative preferred embodiments have one or more inlets 3 which comprise a membrane, which is adapted to be punctured and/or which has an orifice.

The two outlets 4 provided in the preferred embodiment have a circular shape. Yet, again other shapes and sizes are also encompassed by the present invention. The outlets 4 may, e.g., be oval, rectangular, quadratic, triangular, starshaped or have any other shape. While this is not necessary in the context of the present invention, it is preferred that the outlets 4 are smaller, preferably substantially smaller, than the inlets 3, since a flowing stream of the second material has to be inserted through the inlets 3 into the cavity 2, while only gas has to escape through the outlets 4.

Figure 5:
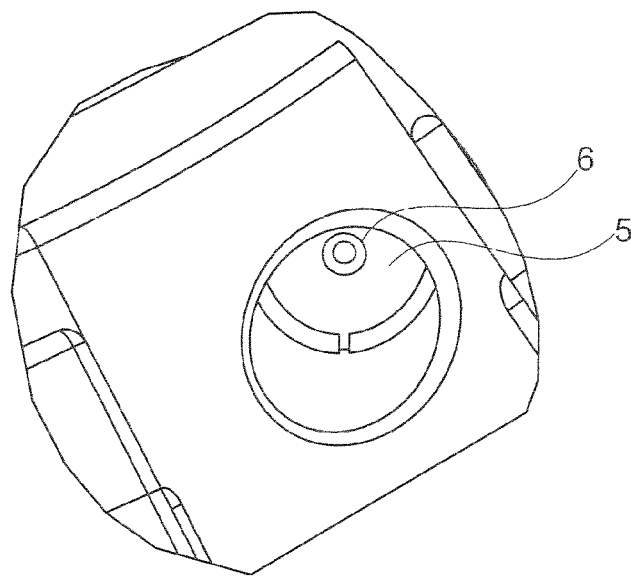

In the preferred embodiment, the outlets 4 each comprise a membrane 5, which is adapted to be punctured. For this purpose, the membrane 5 comprises a predetermined breaking point 6 in the shape of a crossed slot as shown in FIG. 3c. Of course, the predetermined breaking point may have other shapes such as a cross recess, a weakened region or a perforation. Preferred embodiments of membranes 5 are shown in FIGS. 4 and 5 having predetermined breaking points 6 in the shape of a linear slot and a dot, respectively. Moreover, rather than being adapted to be punctured, the membrane may have an orifice, which preferably has a structure adapted to bias the membrane to a closed position.

While the hollow structure according to the preferred embodiment comprises two outlets 4, alternative preferred embodiments may have a single outlet 4 only or more than two outlets such as three or four outlets. In the preferred embodiment, an outlet 4 is provided for each inlet 3, respectively. This is advantageous, since the cavity 2 of the preferred embodiment has two dead ends which terminate exactly below the outlets 4. Since gas may be trapped in such dead ends the two outlets 4 allow for the egress of air through the punctured membrane 5 thus avoiding any air bubbles in the dead ends of the cavity 2.

In order to avoid the formation of any air bubbles within the cavity 2 it is preferred to arrange the hollow structure during the filling process in such a manner that the outlet(s) 4 is/are provided at the top most end(s) of the cavity 2. Thus, gas may escape through the outlet(s) 4 until the entire cavity 2 is filled all the way up to the outlet(s) 4. In case of a more complex shape of the cavity 2, it may be advantageous to tilt the hollow structure during the process of filling.

As is evident from the above, the hollow structure according to the present invention is advantageous in that it allows for an easy and cost-efficient filling of the cavity 2 with a second material while effectively preventing the formation of any trapped gas or gas bubbles. The preferred embodiment only shows a very specific hollow structure. The person skilled in the art will understand that the hollow structure as such may have an entirely different shape. Moreover, the number, shape and size of both the inlets and the outlets may vary strongly without departing from the scope of the present invention. Moreover, only the inlet(s) or only the outlet(s) or both the inlet(s) and the outlet(s) may comprise a membrane. A membrane may be adapted to be punctured and/or have an orifice. Both the membranes of the inlet and the outlet may be adapted to be punctured or have an orifice. Alternatively, the membrane of one of the inlet and the outlet may be adapted to be punctured and the other membrane may have an orifice. While the hollow structure of the preferred embodiment is a cushion for a respiratory mask (once the cavity is filled with the second material), the hollow structure according to the present invention may be any hollow structure which needs to be filled with a second material.

While the technology has been illustrated and described in detail in the drawings and foregoing description, such illustration and description are to be considered illustrative or exemplary and non-restrictive; the invention is thus not limited to the disclosed aspects. Variations to the disclosed aspects can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The disclosed technology also relates to the exact terms, features, numerical values or ranges if the specification above refers to these together with expressions such as 'about', 'substantially', 'at least' and vice versa. For example, "about three" is understood to encompass "3" and "exactly 3" while "substantially radial" is understood to encompass "radial" and "exactly radial". The mere fact that certain measures are recited in mutually different dependent claims does not indicate that a combination of these measures can not be used to advantage. Any reference signs in the claims should not be considered as limiting the scope.

The invention claimed is:

1. Method for producing a filled hollow structure, comprising:
   a) producing a hollow structure of a first material having a cavity, the hollow structure having an inlet to and an outlet from the cavity, the inlet and outlet being separate and spaced from one another;
   b) positioning the hollow structure on a tool for holding the hollow structure;
   c) inserting a second material through the inlet into the cavity, while at the same time allowing gas present in the cavity to escape through the outlet; and
   d) sealing the inlet and/or the outlet;
   wherein the outlet resists or prevents flow of the second material through the outlet during insertion of the second material into the cavity.

2. Method according to claim 1, wherein the inlet and/or outlet comprises a membrane, which has an orifice in the shape of a crossed slot.

3. Method according to claim 1, wherein the second material has a viscosity in a range between 50 and 2000 MPas at 25° C. (DIN EN ISO 3219).

4. Method according to claim 1, wherein the inserted material is distributed within the cavity by means of gravity.

5. Method according to claim 1, wherein the hollow structure is pivoted or tilted during inserting the second material in order to completely fill the cavity with the second material.

6. Method according to claim 1, further comprising sealing the inlet and/or outlet by curing and/or hardening the second material.

7. Method according to claim 1, further comprising sealing the inlet and/or outlet by applying a sealing material.

8. Method according to claim 1, wherein the first material consists of or comprises one or a combination of silicone, polysiloxane, silicone foam, silicone rubber and thermoplastic polymers.

9. Method according to claim 1, wherein the second material consists of or comprises one or a combination of gel, foam, liquid, gas, beads and silicone.

10. Method according to claim 1, wherein the shore hardness of the second material lies in a range between 10 and 20 according to DIN 53505.

11. Method according to claim 1, further comprising removing the hollow structure from the tool by using compressed air.

12. Method according to claim 1, wherein the second material is inserted into the cavity under pressure and/or vacuum.

13. Method according to claim 1, wherein the hollow structure is a cushion for a breathing mask.

14. Method according to claim 1, wherein the inlet and/or outlet comprises a membrane, which is adapted to be punctured.

15. Method according to claim 14, further comprising puncturing the membrane before inserting the second material through the inlet.

16. Method according to claim 14, wherein the membrane comprises a predetermined breaking point in the form of a crossed slot, a cross recess, a weakened region or a perforation.

17. Method according to claim 14, wherein the membrane allows for venting, yet resists or prevents, flow of the second material during insertion into the cavity.

18. Method according to claim 14, wherein the membrane prevents flow of the second material if exposed to a pressure up to 3 hPa.

19. Method according to claim 14, wherein the membrane prevents flow of a material having a viscosity in a range between 50 and 2000 MPas at 25° C. (DIN EN ISO 3219) if exposed to a pressure up to 3 hPa.

20. Method according to claim 14, wherein the flow rate of a material having a viscosity in a range between 50 and 2000 MPas at 25° C. (DIN EN ISO 3219) if exposed to a pressure up to 3 hPa through the membrane is smaller than 100 mm$^3$/s.

21. Method according to claim 14, wherein the membrane has a diameter of less than 5 mm.

22. Method according to claim 14, wherein the orifice of the membrane or the opening in the membrane created by puncturing the membrane has a diameter of less than 4 mm.

23. Hollow structure made of a first material having a cavity, the structure comprising an inlet for inserting a second material into the cavity and an outlet for gas present in the cavity to escape, the outlet being separate from and spaced from the inlet, wherein the inlet and/or outlet comprises a membrane, which is adapted to be punctured and/or which has an orifice.

24. Hollow structure according to claim 23, wherein the punctured membrane and/or the orifice has a structure adapted to bias the membrane to a closed position.

25. Hollow structure according to claim 23, wherein the orifice has the shape of a crossed slot.

26. Hollow structure according to claim 23, wherein the membrane comprises a predetermined breaking point in the form of a crossed slot, a cross recess, a weakened region or a perforation.

27. Hollow structure according to claim 23, wherein the punctured membrane and/or the orifice of the membrane allows for venting, yet resists flow of a material having a viscosity in a range between 50 and 2000 MPas, at 25° C. (DIN EN ISO 3219) if exposed to a pressure up to 3 hPa.

28. Hollow structure according to claim 23, wherein the flow rate of a material having a viscosity in a range between 50 and 2000 MPas at 25° C. (DIN EN ISO 3219) if exposed to a pressure up to 3 hPa through the (punctured) membrane is smaller than 100 mm$^3$/s.

29. Hollow structure according to claim 23, wherein the membrane has a diameter of less than 5 mm.

30. Hollow structure according to claim 23, wherein the orifice of the membrane or the opening in the membrane created by puncturing the membrane has a diameter of less than 4 mm.

31. Hollow structure according to claim 23, wherein the self-healing membrane comprises a predetermined breaking point, preferably a crossed slot, a cross recess, a weakened region or a perforation.

32. Cushion for a respiratory mask comprising a hollow structure according to claim 23, wherein the cavity is filled with the second material.

33. Hollow structure according to claim 23, wherein the outlet orifice has a size that is smaller than a size of the inlet orifice.

34. Hollow structure according to claim 23, wherein the inlet and outlet are structured such that gas present in the cavity escapes at the same time as the second material is introduced into the cavity.

35. Hollow structure according to claim 23, wherein the outlet is structured to allow flow of gas but resist flow of the second material.

36. Hollow structure made of a first material having a cavity, the structure comprising an inlet for inserting a second material into the cavity and an outlet for gas present in the cavity to escape, the outlet being separate and spaced away from the inlet, wherein the inlet and/or outlet comprises a self-healing membrane.

37. Hollow structure according to claim 36, wherein the self-healing membrane is adapted to be punctured in such a manner as to allow for the puncture site to self-seal upon insertion of the second material into the cavity.

38. Hollow structure according to claim 36, wherein the self-healing membrane is adapted to be punctured by a puncturing tool in such a manner as to allow for the puncture site to self-seal upon removal of the puncturing tool.

39. Hollow structure according to claim 38, wherein the punctured membrane and/or the orifice has a structure adapted to bias the membrane to a closed position.

40. Hollow structure according to claim 36, wherein the self-healing membrane has an orifice which is adapted to self-seal upon insertion of the second material into the cavity.

41. Hollow structure according to claim 40, wherein the orifice has the shape of a crossed slot.

* * * * *